United States Patent [19]

Kyle

[11] Patent Number: 4,760,844
[45] Date of Patent: Aug. 2, 1988

[54] CANNULATED SCREW DYE INJECTOR

[75] Inventor: Richard F. Kyle, Minneapolis, Minn.

[73] Assignee: Ace Medical Company, Los Angeles, Calif.

[21] Appl. No.: 132,624

[22] Filed: Dec. 4, 1987

Related U.S. Application Data

[63] Continuation of Ser. No. 842,283, Mar. 21, 1986, abandoned.

[51] Int. Cl.⁴ ............................................. A61F 5/01
[52] U.S. Cl. .......................... 128/92 YQ; 128/92 VP; 128/92 YV
[58] Field of Search ........... 128/92 VP, 92 VQ, 92 R, 128/92 YK, 92 YV

[56] References Cited

U.S. PATENT DOCUMENTS

| | | | |
|---|---|---|---|
| 2,612,159 | 9/1952 | Collison | 128/92 YV |
| 2,702,543 | 2/1955 | Pugh et al. | 128/92 YV |
| 3,223,083 | 12/1965 | Cobey | 128/92 VQ |
| 3,374,786 | 3/1968 | Collender, Jr. | 128/92 YV |
| 3,741,204 | 6/1973 | Thiele | 128/92 VQ |
| 4,261,350 | 4/1981 | Branemark et al. | 128/92 YQ |
| 4,341,691 | 7/1982 | Anuta | 128/92 VP |
| 4,494,535 | 1/1985 | Haig | 128/92 VP |
| 4,595,006 | 6/1986 | Burke et al. | 128/92 VQ |

OTHER PUBLICATIONS

Zimmer, Warsaw IN, 1983 catalog supplement, pp. S21-S22, LVC ® (Low Viscosity Cement).

*Primary Examiner*—C. Fred Rosenbaum
*Assistant Examiner*—Colleen M. Reilly
*Attorney, Agent, or Firm*—Grant L. Hubbard

[57] ABSTRACT

A dye injector apparatus is operatively disposed between a syringe containing an opaque dye suitable for x-ray photography and a cannulated screw or an orthopedic hip fixation device implanted in the ball head of a femur fractured at the femur neck. The dye injector comprises a cannulated shaft, a flange end suitably formed to receive the spout of the syringe, and a needle end suitably formed for insertion into the fixation device. The dye injector communicates the dye from the syringe to the cannulated screw. If the cannulated screw has extended beyond the femur ball head and penetrated the hip socket, an x-ray photograph of the hip socket shows the presence of the dye in the hip socket signaling the need for further operative care so that the cannulated screw will not postoperatively injure the hip socket.

2 Claims, 1 Drawing Sheet

CANNULATED SCREW DYE INJECTOR

This is a continuation of now abandoned application Ser. No. 842,283 filed on Mar. 21, 1986.

BACKGROUND

The present invention relates to orthopedic instruments and more particularly to an apparatus used to evaluate the implantation of femur fixation devices inserted through a fractured neck of a femur bone.

Hip fractures are comparatively common where the femur bone is fractured in the neck or in the ball head. A great many devices have been proposed for the reduction of fractures of this type. A fracture reduction device also known as a orthopedic hop fixation device, may feature a lag screw adapted to be implanated into the ball head of the femur and extended, when in use, through the neck of the femur thereby securely fastening the ball head of the femur to the remaining trochanteric portion of the femur.

An orthopedic hip fixation device is disclosed in U.S. Pat. No. 4,438,762 to Kyle, the inventor of the present invention. U.S. Pat. No. 4,438,762 discloses the structure and use of the orthopedic hip fixation device. The U.S. Pat. No. 4,438,762 is here incorporated by reference as there fully set forth. This prior art patent does not teach a surgeon how to properly select and insert the fixation device respecting the penetration depth into the head ball of a fracture femur bone.

During surgical operations, the orthopedic hip fixation device having a lag screw at one end thereof, is implanted into the femur. The surgeon may have selected a orthopedic hip fixation device which is too large for the patient's femur in the trochanteric area. Or, during implantation, the orthopedic hip fixation device may have been implanted too far into the femur ball head. Consequently, during implantation of the orthopedic hip fixation device, the lag screw may break out of the femur ball head and penetrate into the socket area of the hip joint. During post operative rehabilitation, the patient may have the socket joint damaged by virtue of the lag screw extending into socket tissues of the hip joint. The medical surgeon may not know at time of surgery whether or not the lag screw end of an orthopedic hip fixation device has entered the hip joint area. Thus, the surgeon may not know whether or not the patient will be subjected to post operative damage to the socket tissues when selecting an orthopedic hip fixation device that is too large or when implanting the fixation device too far into the ball head area of the fractured femur bone.

SUMMARY OF THE INVENTION

An object of the present invention is to provide an apparatus and method for enabling surgeons to determine whether or not an orthopedic hip fixation device has been properly implanted into the femur of a patient, which femur has a fractured neck portion.

It is a further object of the present invention to provide an apparatus for injecting dye into and through an orthopedic hip fixation device, during surgery, and possibly into the hip joint socket area so that upon photographic view of the hip socket area, the surgeon can determine whether or not the orthopedic hip fixation device has extended into the hip socket.

It is yet another object of the present invention to prevent injury to the hip socket of patients having orthopedic hip fixation devices implanted into the trochanteric area of the femur having a fractured neck.

An orthopedic fixation device of the kind disclosed in U.S. Pat. No. 4,438,762 comprises a long cylindrical shaft between a distal end and a proximal end. The distal end having attached thereto a lag screw used for drilling into the head ball of a femur through the fractured neck. The orthopedic hip fixation device securely fastens the femur ball head to the remaining portion of the femur. The orthopedic hip fixation device has a shaft with a cylindrical passage therethrough. This cannulated hip fixation device also comprises a head suitably formed at the proximal end for receiving wrenches which impart turning motion to the lag screw so as to firmly screw and implant the orthopedic hip fixation device in the trochanteric area of the femur.

During surgical operations, the surgeon may select an orthopedic hip fixation device that is too large for the patient's femur and may implant the device to far into the ball head of the femur resulting in the lag screw end penetrating the hip joint socket through break out of the femur ball head. The present invention provides a cannulated screw dye injector having a long cylindrical shaft with a cylindrical bore therethrough for communicating a photographic radioopague dye. The integral cannulated screw dye injector comprises a flange end specifically formed for receiving a syringe and further comprises a needle end specifically formed and adapted to be inserted into the head end of the orthopedic hip fixation device.

The syringe stores a radioopague dye fluid which is injected through the cannulated screw dye injector which then passes the opague dye into the orthopedic hip fixation device. In the event that the lag screw has indeed penetrated the hip joint socket, the opague dye is then passed into the joint socket area by virtue of its communication under pressure from the syringe through the cannulated screw dye injector and then through the orthopedic hip fixation device.

X-ray photography or fluoroscopy may film or display the joint hip socket during surgery subsequent to the application of the opague dye so as to determine whether or not there has been a break out by the lag screw from the femur ball head into the joint socket. As such, a surgeon can then determine whether or not there has been break out and whether or not another orthopedic hip fixation device should be implanted so as to prevent post operative damage to the hip socket by a penetrating lag screw. These and other advantages will become more apparent in the following description of the preferred embodiment.

DRAWING DESCRIPTIONS

PREFERRED EMBODIMENT

Figures 1, 2:
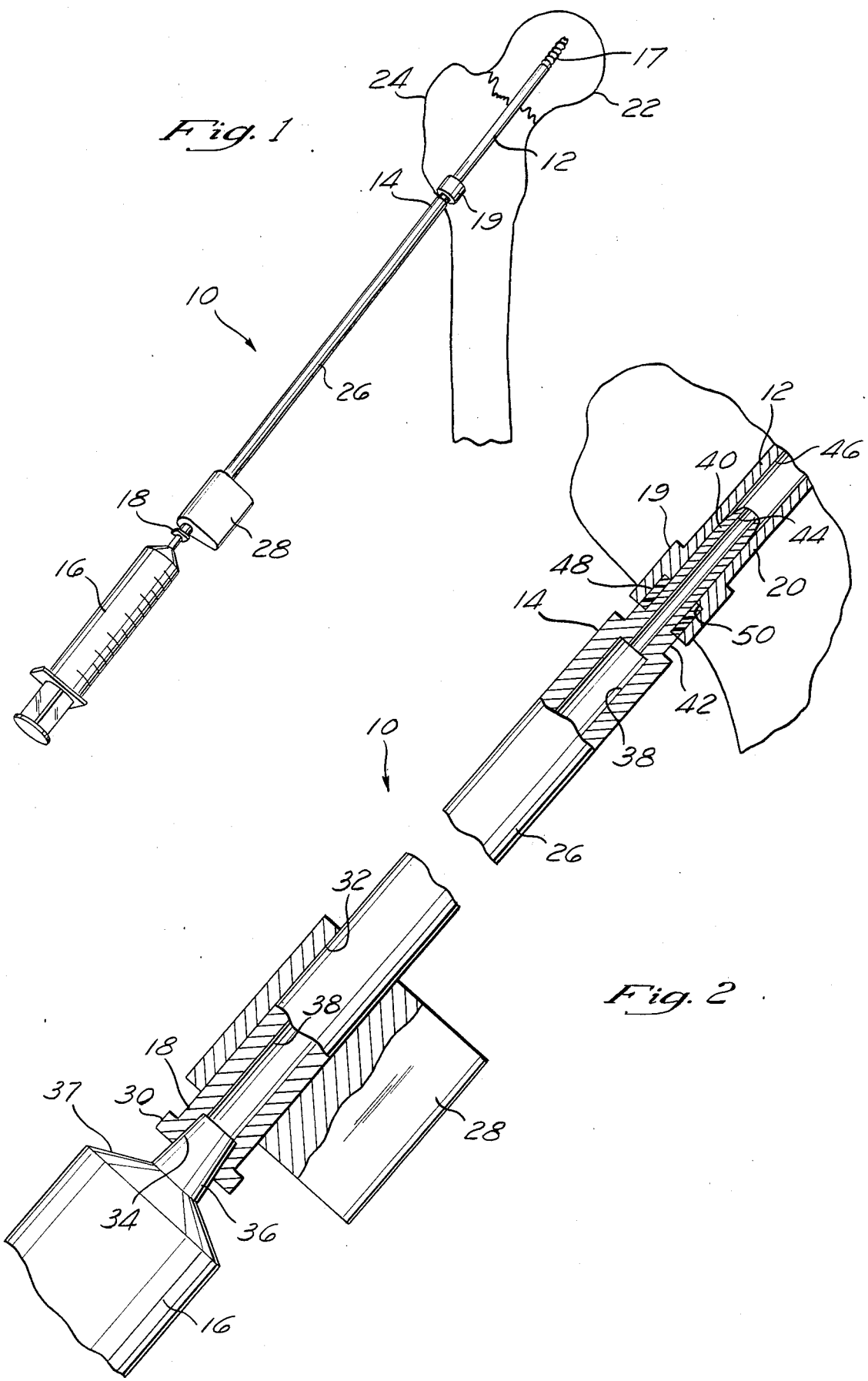
FIG. 1 depicts a cannulated screw dye injector buttressed between a syringe and an implanted orthopedic hip fixation device having a lag screw penetrating into a femur ball head.
FIG. 2 is a detailed diagram depicting the syringe and the orthopedic hip fixation device buttressing respective ends of the cannulated screw dye injector.

Referring to FIG. 1, a cannulated screw dye injector 10 is connected to a cannulated orthopedic hip fixation device 12 at a needle end 14 and is also connected to a syringe 16 at a flange end 18. The fixation device 12 has a lag screw 17 at a distal end and has a head 19 at a proximal end with a cannulated shaft 20 therebetween.

The fixation device 12 securely fastens a femur ball head 22 to the remaining trochanteric portion of the femur 24 by virtue of screwing action upon the lag screw 17 compressing the femur ball head 22 against the femur 24.

The head 19 is suitably formed for receiving wrench apparatus (not shown) imparting turning motion to the lag screw, thereby facilitating the screwing action of the fixation device 12. The femur ball head 22 fits and rotates in the patient's hip socket (not shown). The cannulated screw dye injector 10 has a cannulated shaft 26 between the needle end 14 and the flange end 18. In proximal relation to the flange end 18, a handle 28 is integrally formed therewith for manual manipulation of the cannulated dye screw injector 10.

Referring to FIGS. 1 and 2, the flange end 18 of the cannulated screw dye injector 10 has a flange 30 in close proximity to the handle 28. The handle 28 has a cylindrical bore 32 through which passes the shaft 26 of the cannulated screw dye injector 10. The flange end 18 has a cone shape cavity 34 formed for receiving a syringe spout 36 of the syringe 16.

The cavity 34 may be formed in a variety of shapes, particularly suitable for receiving one of a variety of correspondingly shaped syringe spouts 36. As examples, the cavity 34 may take on the shape of a cone or a cylinder. The penetration of the cavity 34 into the shaft 26 may take on differing depths correspondingly to differing lengths of the syringe spout 36. The flange 30 and the cavity 34 may be specifically designed so that the flange portion 30 buttresses the syringe 16 at a syringe end 37 so as to prevent further penetration of the spout 36 into the cavity 34. The designs of the particularly shaped cavity 34 and corresponding flange end 18 are primarily intended to provide a leak proof seal upon insertion by manual pressure of the syringe 16 into the cavity 34 of the flange end 18.

The shaft 26 of the cannulated dye injector 10 has a cylindrical cavity 38 which extends through the shaft 26 from the cavity 34 to the needle end 14. The needle end 14 comprises a needle 40 and an intermediate diameter portion 42, both of which having therein a cylindrical cavity 44 which communicates fluid between the cylindrical cavity 38 and a cylindrical cavity 46 of the shaft 20 of the cannulated orthopedic hip fixation device 12.

A plastic sleeve 48 is concentrically circumferentially disposed about the needle 40 while buttressing the intermediate diameter portion 42. When the needle 40 is inserted into the cannulated orthopedic hip fixation device 12, the plastic sleeve 48 buttresses against a cavity 50 of the head 19 of the fixation device 12. The cavity 50 of the hip fixation device 12 may have a hexagonal shape, a cylindrical shape or an other suitable shape adapted to fit within the keeper 19. The plastic sleeve 48 acts as a small pliable plastic sealing gasket reducing fluid discharge or gas leakage between the dye injector 10 and the fixation device 12.

INDUSTRIAL APPLICATION

This invention is used in orthopedic surgery. In operation, the cannulated hip screw dye injector 10 is used in buttress relation with the cannulated fixation device 12. The dye injector 10 is inserted into the head end 14 of the fixation device 12, while the syringe 16 is inserted into the flange end 18. The syringe 16 containing a radio opague dye, injects the dye under pressure through the dye injector 10 into the cannulated hip fixation device 12. If the femur ball head 22 has been penetrated by the lag screw 16 to the extent that the lag screw 16 extends into the joint socket of the patient's hip, the radio opague dye is then also injected into the hip socket. Radio opague dye in the ball joint socket of the hip will be visible through an x-ray or an intensification x-ray device such as a fluoroscope.

During implantation of the fixation device 12, a surgeon can view the x-ray device and determine whether or not the ball joint socket has been penetrated by the lag screw 16. In such an event, the surgeon can take corrective action so that the lag screw 16 is not embedded into the joint socket thereby preventing post operative damage to the joint socket of the hip.

Even though those skilled in the art may conceive or invent differing cannulated screw dye injectors designs or modifications, those designs and modifications may never the less represent applications and principles within the spirit and scope of the present invention as defined by the following claims.

What is claimed is:

1. A method of determining break out of a orthopedic hip fixation cannulated lag screw having threads and a cannula opening at a distal and a head at a proximal end extending through the ball head portion of a femur bone, comprising the steps of:

implanting said orthopedic hip fixation cannulated lag screw into said ball head portion of said femur bone;

inserting a needle end of a cannulated screw dye injector into a head end of said orthopedic hip fixation cannulated lag screw;

inserting a syringe filled with a dye into a flange end of said cannulated screw dye injector;

communicating said dye under pressure from said syringe, through said cannulated screw dye injector, through said cannula opening of said orthopedic hip fixation cannulated lag screw, and possibly into a hip socket; and photographing said hip socket for the presence of said dye in said hip socket.

2. A surgical injection system for determining break out of a femur ball head comprising:

an implanted orthopedic hip fixation cannulated lag screw having threads and a cannula opening at a distal and a head at a proximal end;

a cannulated screw dye injector having a needle end inserted into said head and having a flange end; and a syringe having a spout inserted into said flange end for communicating a dye under pressure through said cannulated screw dye injector, through said implanted orthopedic hip fixation cannulated lag screw and possibly through said break out.

* * * * *